(12) United States Patent
Perry

(10) Patent No.: US 7,344,728 B1
(45) Date of Patent: Mar. 18, 2008

(54) INSECT REPELLENT WITH SUN PROTECTION FACTOR

(76) Inventor: Stephen C. Perry, 205 Churchill Dr., Longwood, FL (US) 32779

( * ) Notice: Subject to any disclaimer, the term of this patent is extended or adjusted under 35 U.S.C. 154(b) by 711 days.

(21) Appl. No.: 10/248,584

(22) Filed: Jan. 30, 2003

(51) Int. Cl.
    *A01N 25/32* (2006.01)

(52) U.S. Cl. .................. 424/406; 424/59; 424/195.18; 424/736; 424/742; 424/750; 424/761; 424/767; 424/770; 424/DIG. 10; 514/919

(58) Field of Classification Search ............... 424/405, 424/195.18, 725, 736, 742, 750, 761, 767, 424/770
See application file for complete search history.

(56) References Cited

U.S. PATENT DOCUMENTS

| | | | |
|---|---|---|---|
| 4,164,561 A | | 8/1979 | Hautmann |
| 4,361,554 A | * | 11/1982 | Saunders .................... 424/767 |
| 5,594,029 A | | 1/1997 | Bencsits |
| 5,621,013 A | | 4/1997 | Beldock et al. |
| 5,716,602 A | * | 2/1998 | Uick ............................ 424/59 |
| 5,885,600 A | * | 3/1999 | Blum et al. .................. 424/405 |
| 5,916,541 A | * | 6/1999 | Stewart ........................ 424/59 |
| 6,143,288 A | * | 11/2000 | Warren et al. ................ 424/84 |

FOREIGN PATENT DOCUMENTS

CH      688787     *    3/1998

OTHER PUBLICATIONS

Merck Index, 1968 p. 759.*
Gardners Chemical Synonyms- p. 263., 1994.*

* cited by examiner

*Primary Examiner*—Neil S. Levy
(74) *Attorney, Agent, or Firm*—Malin Haley DiMaggio Bowen & Lhota, P.A.

(57) ABSTRACT

An insect repellent composition that includes a blend of either all natural oils or synthetic ingredients, a sunscreen vitamin F, volatile silicones to extend the effective repellent life of the spray and a film forming polymer to resist water wash off. The natural oils and extracts can include citronella and orange and the synthetics can include D-limonene and phtalic acid.

4 Claims, No Drawings

INSECT REPELLENT WITH SUN PROTECTION FACTOR

BACKGROUND OF INVENTION

1. Field of the Invention

This invention relates generally to an insect repellent (either in a lotion, spray, cream, gel, salve, solid stick or ointment) for human beings and animals, and specifically, to a topical insect repellent that may include sun screen and that may be made with natural oils or botanical extracts, an additive to increase the time of repellent effectiveness and a film forming polymer to make the lotion more resistant to being washed off the skin with water, making the composition rain and sweat resistant once applied to the skin.

2. Description of Related Art

Insect repellents for human beings and domestic animals, especially pets, are well known in the art. Historically, original insect repellents often contain high levels of sometime toxic chemicals and were not medically good for skin contact in human beings or pets. Outdoor environments enjoyed by humans such as tropical climates, beaches or lakes include activities in direct sunlight. Insects are often present in these environments.

One problem with insect sprays or lotions is lack of water/sweat tolerance. Sweating, rain, and swimming tend to wash off, dissolve or evaporate the repellent from the skin of the user. Several applications of insect spray would be required over short periods of time in order to be effective. Another problem with insect repellents is that their effective insect repelling time period, once applied to the skin, is relatively short.

As stated above, many of the original insect repellents not only were toxic to insects but to human beings too. It would be desirable to provide an insect repellent that is not only not harmful to humans (such as skin rashes), but that would have a positive health effect for either enhancing the skin of the human or helping the skin by providing for good skin care.

Obviously it is most important for an insect repellent to ward off insects, preferably both as to human skin and to domestic animal furs and skins. In order to accomplish other important goals such as being healthy for a human being or enhancing the staying power of the insect repellent on the human skin, it is important not to reduce or cancel the efficacy of the insect repellent.

Use of natural substances in insect repellents are known in the prior art. U.S. Pat. No. 5,594,029 issued Jan. 14, 1997 describes an insect repellent that uses coconut fatty acid for repelling biting and flying insects. U.S. Pat. No. 4,164,561 issued Aug. 14, 1979 describes an insect repellent that uses synthetic elements for repelling insects.

U.S. Pat. No. 5,621,013 issued Apr. 15, 1997 describes an insect repellent that uses a blend of primarily natural substances. None of the references shown in the prior art provide the scope of insect repellent coverage provided by the present invention including the longer lasting effectiveness of the repellent and its durability of staying on the skin in spite of a wet environment.

The present invention provides an improved insect repellent that can be topically applied as a lotion, spray, cream, gel, salve, solid stick or ointment that includes the use of a blend of natural oils in combination with one or more vitamins, a specific insect repellent ingredient such as phthalic acid, the use of volatile silicone to extend the skin time efficacy to ward off insects and finally the use of a film forming polymer which prevents the insect repellent from washing off the skin either from sweat or rain or water activities. In an alternate embodiment, a sun screen with high SPF may be added without reducing the efficacy of the repellent.

SUMMARY OF INVENTION

An insect repellent that is healthy for the skin that includes a composition having a blend of natural oil extracts to aid in warding off insects, vitamin F, phthalic acid, a volatile silicone to extend the skin time efficacy of the insect repellent and a film forming polymer for water wash off resistance making it rain and sweat resistant.

In an alternate embodiment of the invention, synthetic insect repellent ingredients can be used as a blend with or in place of natural oils. In yet another embodiment a sun protection factor (SPF) complex chemical to provide sun screen protection is employed.

The oils or extracts used in the natural version as a blend can be citronella oil, orange oil, eucalyptus oil, eucalyptus extract, cedarwood oil, pine oil, camphor oil, lemon oil, prickly pear juice, linalool, D-limonene, geraniol, neem oil, linaloe wood oil and eucalyptol.

The volatile silicones in the composition are dimethicone or cyclomethicone. These are used to enhance or prolong the effective use of the insect warding off chemicals in the oils.

A film forming polymer is used to make the insect repellent lotion or spray adhere to the skin or fur to prevent being washed off by water, making the insect repellent rain and sweat resistant. This polymer can be PVM/MA copolymer or butyl ester of PVM/MA co-polymer or isopropyl ester of PVM/MA co-polymer. The ethyl ester of PVM/MA co-polymer is preferred.

In an alternate embodiment, the insect repellent compounds in lieu of being natural version oil extracts could be synthetics that would be used as a replacement for the natural oils discussed above. The following synthetics are used which include linalyl acetate, l-limonene, cineole, phthalic acid or dimethyl phthalate, eugenol, and eugenyl acetate.

The insect repellent can be manufactured as a lotion, spray, gel, salve, cream, solid stick or ointment for application purposes.

In the preferred embodiment, using natural oils, the materials are combined to provide for an insect repellent that includes vitamin F and a volatile silicone to extend the shelf life of the insect repellent chemicals or natural oils and a film forming polymer on the skin to prevent the insect repellent from being washed off the skin. With the use of the composition described herein, the product can be used for humans, pets and livestock. It is a long lasting, very effective insect repellent that may include sun screen to prevent skin damage from the sun.

In an alternate embodiment, a sun screen SPF complex is added. The SPF complex would be octyl methoxycinnamate (7.5% by weight); benzophenone-3 (5.0% weight); octyl salicylate (3% weight). This is a preferred sunscreen complex for an SPF-30. Other SPF ingredients can be used, and different SPF values can be obtained for use with the insect repellent.

It is therefore an object of the present invention to provide an insect repellent for application to the skin of a person or pet using a blend of natural or synthetic materials with the least toxicological risk and as a high efficacy over a long period of time without easily being removed from the skin of the user.

It is another object of this invention to provide an insect repellent and sun screen that is non-toxic for the skin of human beings and the skin and fur of animals including pets and livestock; that is efficient for long periods of time; and that prevents sun light damage to the skin.

It is another important object of this invention to provide an insect repellent and sun screen that does not irritate the human skin or animal skin but at the same time is perspiration resistant.

Another object of invention is to provide an insect repellent that can act against a wide variety of different types of insects, including mosquitoes and flies, while still maintaining the ability to be healthy for human skin.

DETAILED DESCRIPTION

The overall composition of the preferred embodiment is provided with the use of a blend of preferably natural active oils and extracts selected from the following group:

Natural Oils

The blend is comprised of equal parts of each natural oil listed (approximately 7 parts each per hundred parts for the 14 oils listed):

citronella oil, orange oil, eucalyptus oil or eucalyptus extract, cedarwood oil, pine oil, camphor oil, lemon oil, prickly pear juice, linalool, D-limonene, geraniol, neem oil, linaloe wood oil, and eucalyptol. These natural oils are blended together to constitute the oil portion and insect repellent portion in the preferred embodiment. The oil blend does not have to include all 14 oils but should have at least 7 oils listed. These oils can be mixed in various combinations and are effective for repelling certain insects including mosquitoes and flies.

The active natural oils can be employed in weight ratios of 10 percent to 30 percent of the total weight. Preferably fifteen to twenty-five percent and most preferably about 20 percent by weight of the total.

EXAMPLE NO. 1

Includes SPF-30 Sun Screen

20% by weight of a natural oil blend comprising:
citronella oil at 50 parts
eucalyptus at 12.5 parts
prickly pear at 12.5 parts
D-limonene at 12.5 parts
Cedarwood oil at 12.5 parts
40% by weight of SD alcohol
19.2% by weight cyclomethicone
7.5% by weight of octyl methoxycinnamate
5% by weight of benzophenone-3
3.0% by weight of octyl salicylate
2% by weight of PBM/MA co-polymer
2% by weight of polysorbate-20
0.50% by weight fragrance
0.25% by weight orange oil
0.25% by weight vitamin-E
0.3% by weight aloe extract The Example No. 1 preferred embodiment uses the natural oils and extracts as the insect repellent. The SPF sun screen complex chemicals comprise the octyl methoxycinnamate, benzophenone-3 and the octyl salicylate. The SPF complex components can be different, but these are preferred. The SD-alcohol acts as a carrier and base for the entire composition for the spray version. The cyclomethicone is used a volatile silicone to extend the life of the insect repellent oils. The PMB/MA co-polymer is used to provide a film forming polymer that makes it difficult to wash off or sweat off the insect repellent and sun screen during normal use out doors. The aloe and vitamin E is used as a skin conditioner and a skin protector. The SD-alcohol is a sugar derived emulsifier and food grade alcohol that is used as a carrier complex.

To use the composition as disclosed in Example 1 as an insect spray and sun screen, the user would spray the composition on the skin of the user or on the skin or fur of an animal or possibly even on clothing to ward off insects. The composition also functions as a sun screen that has an SPF of 30.

In an alternate embodiment a lotion can be prepared that does not include sun screen. The advantage of this it is a superior insect spray, it can use natural or synthetic insect repellents as active ingredients and it includes volatile silicones for extending the effective use of the insect repellent components while at the same time using a polymer for a water resistant film coating on the skin. It can also use vitamins and skin conditioners.

EXAMPLE NO. 2

No Sunscreen 28.0% by weight of a natural insect repelling oil blend selected from the natural oil blend listed above under "Natural Oils."
3.0% by weight of glycerol stearate and PEG-100 stearate.
2.0% by weight of propylene glycol.
1.0% by weight of cyclomethicone.
0.3% by weight of diazolidinylurea.
0.3% by weight of tetrasodium EDTA.
0.2% by weight of polymeric emulsifier.
0.2% by weight of methyl paraben.
0.15% by weight of triethanolamine.
0.1% by weight preservative.
0.1% by weight proplyparaben.
64.65% by weight water.

The cyclomethicone is a volatile silicone that extends the life of the insect repelling oils. The polymeric emulsifier provides for the use of a film forming polymer for water wash off resistance making the composition rain and sweat resistant.

EXAMPLE NO. 3

Replace the natural insect repelling natural oil blend which is 28.0% by weight in Example No. 2 with the following blend in equal parts of the synthethics: linalyl acetate; L-limonene; cineole; phthalic acid or dimethyl phthalate; eugenol; and eugenyl acetate. The volatile silicone used could be replaced also from a cyclomethicone dimethicone. With respect to the polymer used is can be PVM/MA co-polymer or butyl ester of PVM/MA co-polymer or isopropyl ester of PVM/MA co-polymer. The ethyl ester of PVM/MA co-polymer is preferred.

The synthetic oils employed should constitute ten to thirty percent by weight of the total composition. Fifteen to twenty-five percent is preferred and about twenty percent is most preferable. The synthetic compounds are blended in equal parts to make up the total synthetic blend used.

The insect repellent and sun spray composition or the insect repellent alone can be prepared by mixing the ingredients described above at room temperature and stirring the ingredients.

Thus the insect repellent in accordance with the present invention can be all natural or can be a blend of all natural oils and extracts or can be a blend that includes synthethic ingredients as well as all natural oils or extracts. In the preferred embodiment the insect repellent includes the sun screen that is preferably an SPF 30 protective for human and animal skin. The present invention also includes the use of volatile silicones that extends the life of the insect repellent oils once they are applied to the skin of the human or the animal. Vitamins are also used for enhancing the skin and a film forming polymer to resist washing off making it rain and sweat resistance is employed.

In the preferred embodiment an insect repellent and sun screen that is a spray on is the preferred embodiment as discussed in Example No. 1.

The primary purpose of the invention is to keep insects away using natural oils. A secondary purpose is to combine an insect repellent with a sun screen.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. An insect repellent and sun screen composition comprising blend of the following elements:
    20.0% by weight of a natural oil blend comprising:
        citronella oil eucalyptus oil, prickly pear juice, D-limonene, and lemon oil; and
        one or more of orange oil, eucalyptus extract, cedarwood oil, pine oil, camphor oil, linalool, geraniol, neem oil, linaloe wood oil and eucalyptol;
    40.0% by weight of specially denatured (SD) alcohol 40 (SD-40 alcohol);
    19.2% by weight cyclomethicone;
    7.5% by weight of octyl methoxycinnamate;
    5.0% by weight of benzophenone-3;
    3.0% by weight of octyl salicylate;
    2.0% by weight of polyvinylmethylether maleic anhydride (PVM/MA) co-polymer;
    2.0% by weight of polysorbate-20;
    0.50% by weight fragrance;
    0.25% by weight orange oil;
    0.25% by weight vitamin-E; and
    0.30% by weight aloe extract.

2. The insect repellent and sun screen composition of claim 1, wherein:
    a natural oil blend is such that the natural oils are further comprised of equal parts of each approximately 7 parts of each to make a 100 parts total by volume.

3. The insect repellent and sun screen composition of claim 1, wherein:
    citronella oil, eucalyptus oil, prickly pear juice, D-limonene, and lemon oil comprise the first part of the 20.0% by weight of the natural oil blend and are included in said first part in the following amounts:
    citronella oil at 50 parts;
    eucalyptus oil at 12.5 parts;
    prickly pear juice at 12.5 parts;
    D-limonene at 12.5 parts; and
    lemon oil at 12.5 parts.

4. A method for repelling insects from the surface of human skin or animal skin or fur comprising the step of applying to the skin or fur surface an effective amount of insect repellent composition, said insect repellent composition comprising:
    20.0% by weight of a natural oil blend comprising:
        citronella oil, eucalyptus oil, prickly pear juice, D-limonene, and lemon oil; and
        one or more of orange oil, eucalyptus extract, cedarwood oil, pine oil, camphor oil, linalool, geraniol, neem oil, linaloe wood oil and eucalyptol;
    40.0% by weight of specially denatured (SD) alcohol 40 (SD-40 alcohol);
    19.2% by weight cyclomethicone;
    7.5% by weight of octyl methoxycinnamate;
    5.0% by weight of benzophenone-3;
    3.0% by weight of octyl salicylate;
    2.0% by weight of polyvinylmethylether maleic anhydride (PVM/MA) co-polymer;
    2.0% by weight of polysorbate-20;
    0.50% by weight fragrance;
    0.25% by weight orange oil;
    0.25% by weight vitamin-E; and
    0.30% by weight aloe extract.

* * * * *